United States Patent [19]
Cooper

[11] Patent Number: 5,483,953
[45] Date of Patent: Jan. 16, 1996

[54] AEROSOL DISPENSING APPARATUS FOR DISPENSING A MEDICATED VAPOR INTO THE LUNGS OF A PATIENT

[75] Inventor: Guy F. Cooper, Ventura, Calif.

[73] Assignee: The United States of America as represented by the Secretary of the Navy, Washington, D.C.

[21] Appl. No.: 493,519

[22] Filed: Jun. 22, 1995

Related U.S. Application Data

[63] Continuation-in-part of Ser. No. 437,860, May 8, 1995.
[51] Int. Cl.⁶ .................................................. A61M 11/02
[52] U.S. Cl. ........................... 128/200.22; 128/200.14; 128/203.12; 128/203.29
[58] Field of Search ................... 128/200.14, 200.16, 128/200.22, 200.23, 200.24, 202.21, 203.12, 203.15, 203.23, 203.29; 446/24

[56] References Cited

U.S. PATENT DOCUMENTS

| | | | |
|---|---|---|---|
| 2,788,607 | 4/1957 | Ward | 446/24 |
| 4,090,320 | 5/1978 | Loiacono | 446/24 |
| 4,228,795 | 10/1980 | Babington | 128/200.22 |
| 4,852,561 | 8/1989 | Sperry | 128/200.23 |
| 4,880,147 | 11/1989 | Tolan | 222/195 |
| 5,025,806 | 6/1991 | Palmer et al. | 128/203.12 |
| 5,100,242 | 3/1992 | Latto | 366/267 |
| 5,415,246 | 5/1995 | Cooper | 180/287 |

FOREIGN PATENT DOCUMENTS

| | | | |
|---|---|---|---|
| 91/03270 | 3/1991 | WIPO | 128/203.15 |
| 92/04928 | 4/1992 | WIPO | 128/200.14 |

*Primary Examiner*—Ren Yan
*Assistant Examiner*—Eric P. Raciti
*Attorney, Agent, or Firm*—David S. Kalmbaugh; Melvin J. Sliwka

[57] ABSTRACT

A dispensing apparatus comprising a reservoir for providing a medication under pressure and a housing which has a centrally located chamber and a wave shaping chamber located in a front portion of the housing. Positioned between the wave shaping chamber and the centrally located chamber is a blast valve. The plunger of a reciprocating piston has a vertical extending support member attached its front end. A power supply provides a square wave signal at a predetermined frequency to a coil alternatively energize and de-energize the coil. When the coil is energized the piston moves rearward. De-energizing the coil results in forward movement of the piston. A plurality of inlet ports positioned around the housing between an inlet manifold coupled to the reservoir and the centrally located chamber allow the medication to enter the chamber as a medicated vapor when the piston is drawn rearward. An impact head attached to the piston unseats the blast valve when the piston moves forward allowing medicated vapor to enter the wave shaping chamber. An edged shaped orifice at the front end of the housing communicates with the wave shaping chamber allowing medicated vapor to exit the wave shaping chamber and pass through the edged shaped orifice to form a ring vortex of medicated vapor. The blast valve opens and closes at the predetermined frequency causing the aerosol dispensing apparatus to generate a train of the ring vortices of medicated vapor.

11 Claims, 7 Drawing Sheets

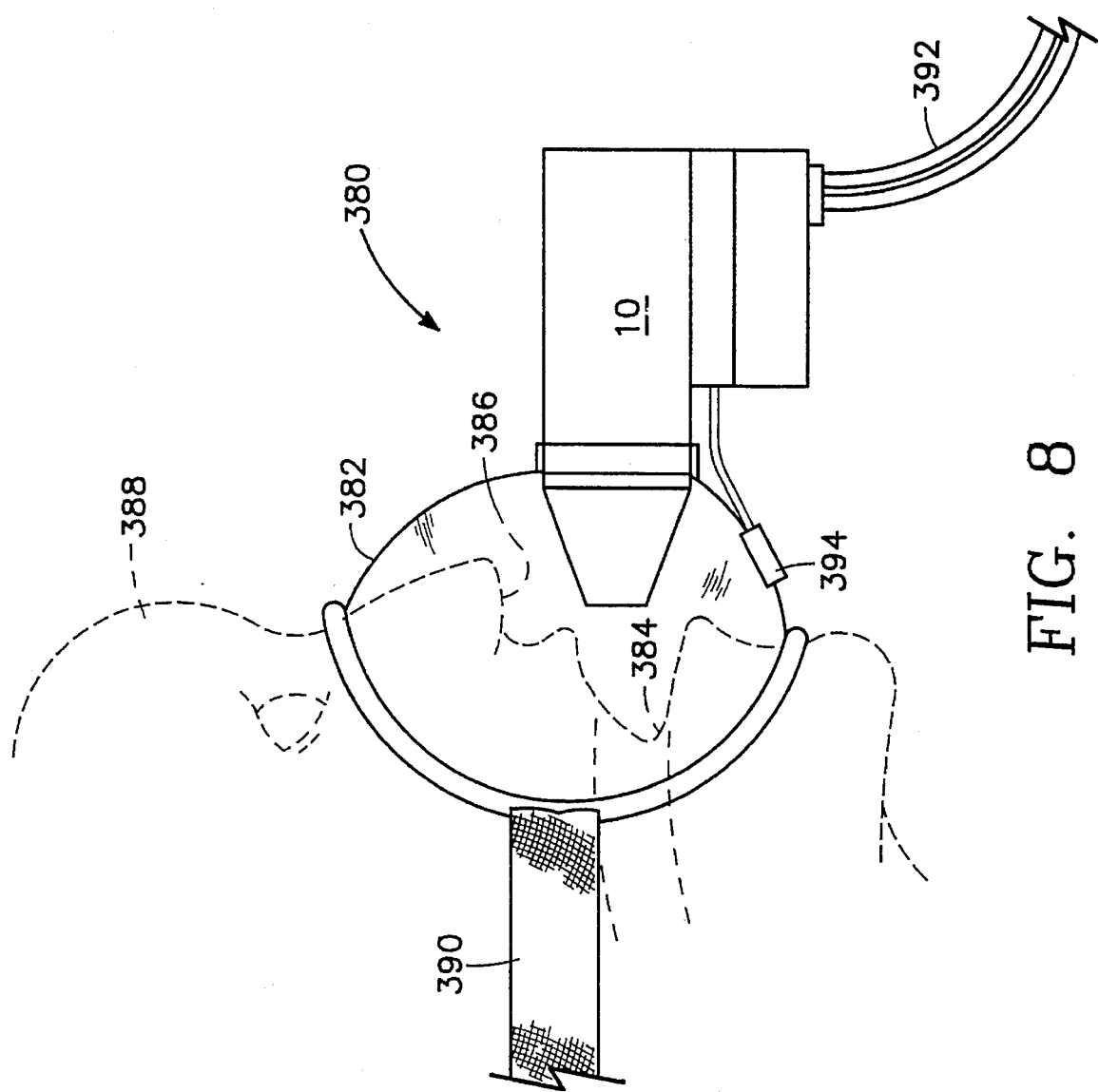

AEROSOL DISPENSING APPARATUS FOR DISPENSING A MEDICATED VAPOR INTO THE LUNGS OF A PATIENT

This application is a continuation-in-part of U.S. patent application Ser. No. 08/437,860, filed May 8, 1995.

BACKGROUND OF THE INVENTION

1. Field of the Invention

The present invention relates generally to medical treatment apparatus. More specifically, the present invention relates to a ring vortex aerosol projection apparatus for providing medication in a vapor form to the lungs of a patient having asthma or a like medical condition.

2. Description of the Prior Art

Patients suffering from asthma or any of the many other lung diseases require delivery of medication to the bronchi in the lungs. At the present time there are three major ways of delivering aerosol treatment or medication to such patients, namely (1) nebulizers, which may be of the (a) venturi-jet type, or of the (b) ultrasonic piezoelectric type which produce aerosols from drug solutions; (2) metered dose inhalers (MDI) consisting of fluorocarbon or other gas pressurized canisters; and (3) dry powder inhalers (DPI) which may be (a) passive or (b) active. Dry powder inhalers also provide metered doses if sufficient suction is supplied by the patient.

Metered dose inhalers which are both MDI and DPI have certain advantages over nebulizers because they are readily portable, and do not generally require an external power source such as compressed air or electricity. Metered dose inhalers are also capable of generating aerosols that are suitable for inhalation, more efficiently, reliably and cost effectively. The pressurized canister type of aerosol generator (MDI) includes a valve, which, when actuated, causes dispersement of a metered quantity of drug.

Because metered dose inhalers have previously used a chlorofluorocarbon as the propellant, and chlorofluorocarbons are believed to have a highly adverse effect on the ozone layer surrounding the earth, they are gradually being phased out to be replaced by the environmentally more friendly hydrofluorocarbons (e.g., HFC 134a and 227).

Such metered dose inhalers have become popular in that a droplet aerosol consisting of the drug particles and the fluorocarbon propellant is generated. The fluorocarbon propellant evaporates rapidly, and leaves smaller drug particles and clumps of particles, at least some of which are on the order of 1–3 microns aerodynamic mass median diameter which is the ideal size range for medication aerosols in humans. Unfortunately, many of the particles remain in larger clumps, and do not reach the necessary areas in the bronchi and lungs.

For example, some metered dose inhalers are relatively inefficient because they produce mainly non-respirable particles that range in size from about 35 micro-meters to about 1 micrometers. Of these particles only about 30 percent, chiefly particles under 5 micrometers, are actually capable of being inhaled. In practice this figure is closer to 20 percent. Most of the rest of the aerosol which is deposited in the throat has the potential for causing side effects, while not contributing to the therapeutic benefit.

There are some currently available powder inhalation systems which do not require a propellant. However, they do not function very effectively unless the patient can generate flow rates greater than 30–60 liters per minute, since it is the energy provided by the patient's forceful inhalation that not only mobilizes the powder but also breaks up the clumps thus preparing it for inhalation, in contrast with the high pressure of the fluorocarbon or other propellant in metered dose inhalers which accomplish the same end.

The patient's inhalation then carries the medication aerosol into the air passages via a mouthpiece. Current powder inhaler systems require strong inhalation on the part of the patient. They have not worked effectively with patients who cannot inhale vigorously.

In the metered dose inhalers noted above, it is common practice to include surfactants such as oleic acid. This presents problems. The fluorocarbon-medication suspension emerges as a liquid jet from the end of the valve stem or from the end of a cannula attached to the valve stem through which the metered dose inhaler contents have been forced and about 80 percent of it is deposited within three or four centimeters of the end of the valve or cannula. This results in an inefficient delivery system. It further has the disadvantage that large amounts of the surfactant material is deposited on the lining of the trachea, and the first few bronchi. It has been demonstrated that this causes injury to the airway lining with ulceration.

Over about the last 25 years systems for delivering medications to the lungs such as aerosol type delivery systems have become increasingly important for the treatment of airway diseases, particularly asthma and chronic obstructive pulmonary diseases, such as chronic bronchitis and emphysema as well as bronchiolitis and bronchiectasis. Other aerosol medications include mucolytic agents to thin secretions, the newest of which is deoxyribonuclease made by a recombinant method (rhDN-ase).

It is becoming increasingly important to deliver antibiotics directly to the airway for chronic illnesses such as cystic fibrosis, for treating a type of pneumonia in immunosuppressed patients (e.g., in AIDS), and for providing a new class of medications (sodium channel blockers) in cystic fibrosis to "lubricate" the secretions and make them easier to cough up or remove as a result of the action of cilia.

Aerosol systems for delivering medication directly to the patient's lungs generally fall into one of two categories, either (1) active or (2) passive. "Active" devices include (a) metered dose inhaler and (b) wet nebulizers. The pressurized canister metered dose inhaler generates the aerosol and directs it towards the patient independently of the patient's force of inhalation. This provides aerosol to the patient in a manner similar to so called "wet nebulizers" that aerosolize a drug solution. These "wet nebulizers" are jet nebulizers using the venturi principle, the energy source being compressed air which also serves to direct aerosol towards the spontaneously breathing or ventilation assisted patient, and ultrasonic nebulizers utilizing high speed vibration of a piezo-electric crystal and a blower fan to carry the medication aerosol to the patient. These are all active aerosol devices, since with the jet nebulizer it is the flow of oxygen or air through the device that creates the aerosol and drives it towards the patient who can then breathe in from a mouthpiece or mask. The ultrasonic nebulizer generates the aerosol into a space from which it can be inhaled by the patient breathing normally to inhale the mist with each inhalation, even if that inhalation is not vigorous. In addition, a blower can be incorporated which pushes the aerosol from the ultrasonic generator toward a mask or mouthpiece from which the patient inhales.

In contrast, currently available powder inhalers are "passive" devices in that the drug powder must reside in a small reservoir from which the patient can suck it by creating a relatively high inspiratory flow rate, usually over 30 liters per minute, and sometimes as high as 90–120 liters per minute if the optimum dose of medication is to be provided. This type of device has the advantage that aerosol is inhaled automatically when the patient inhales vigorously, but has certain disadvantages in that (a) there is considerable variability in dose depending upon how vigorously the patient inhales; (b) during severe episodes of asthma it may not be possible to create the high flow rates necessary to get a full dose of the drug which is particularly true of children under the age of 6; and (c) the greatest efficiency for aerosol inhalation is achieved at low inspiratory flow rates, 45 liters per minute and below, because at high flow rates small particles have greater inertia and therefore act like larger particles, thereby tending to be deposited in the back of the throat and around the larynx by impaction rather than being carried into the airways of the lungs where the medication must be deposited to be effective.

Another disadvantage of some widely prescribed current powder systems relates to exposure to the humidity of the environment of the drug reservoir where the fine particles are stored. Since many drug particles are very hygroscopic, repeated or continual exposure to humidity will greatly reduce the available dose due to swelling and clumping.

In view of the foregoing, what is needed is a relatively simple, yet highly effective dispensing apparatus which will effectively provide medication in a mist or vapor form to the lungs of a patient without requiring the patient to inhale vigorously.

SUMMARY OF THE INVENTION

The present invention overcomes some of the disadvantages of the prior art including those mentioned above in that it comprises a relatively simple yet highly reliable and efficient dispensing apparatus which effectively provides medication in a mist or vapor form to the lungs of a patient without requiring the patient to inhale vigorously.

The dispensing apparatus comprises a reservoir for providing a medication under pressure and a cylindrical shaped housing which has a centrally located chamber and a wave shaping chamber located in a front portion of the housing. Positioned between the wave shaping chamber and the centrally located chamber is a blast valve which rests on a valve seat located within the housing.

The dispensing apparatus includes a support rod which is fixedly attached to the rear wall of the housing and which extends longitudinally forward from the rear wall of the housing. The plunger of a reciprocating piston, which is slidably mounted on the support rod, has a vertical extending support member attached its front end. An impact head is also attached to the front end of the reciprocating piston.

A coil is mounted within a rear portion of the housing. A thin walled cylindrical shaped skirt attached to the piston's support member extends into a recess located between the inner surface of the housing and the coil.

A power supply provides a square wave signal of a frequency between 20 and 100 hertz to the coil alternatively energize and de-energize the coil. When the coil is energized the piston moves in a rearward direction. De-energizing the coil results in the piston moving in a forward direction.

An input manifold positioned around an outer surface of the housing is coupled to the reservoir to receiving the liquid medication from the reservoir. A plurality of inlet ports positioned around the housing between the manifold and the centrally located chamber allow the medication to enter the chamber as a medicated vapor when the piston is drawn in the rearward direction. When the piston moves forward the cylindrical shaped skirt closes the inlet ports preventing the medicated vapor from entering the centrally located chamber.

The impact head unseats the blast valve when the piston moves in the forwarding direction allowing the medicated vapor to enter the wave shaping chamber. An edged shaped orifice at the front end of the housing communicates with the wave shaping chamber allowing the medicated vapor to exit the wave shaping chamber and pass through the edged shaped orifice to form a ring vortex of medicated vapor.

The blast valve opens and closes at the predetermined frequency of the square wave signal causing the aerosol dispensing apparatus to generate a train of the ring vortices of medicated vapor.

A mask is coupled to the front end of the housing with the mask being adapted to cover a patient's mouth and nose, allowing the patient to inhale the train of the ring vortices of medicated vapor.

BRIEF DESCRIPTION OF THE DRAWINGS

FIG. 8 illustrates a mask which may worn by a patient using the aerosol dispensing apparatus of the present invention.

DETAILED DESCRIPTION OF THE PREFERRED EMBODIMENT

Figure 2:
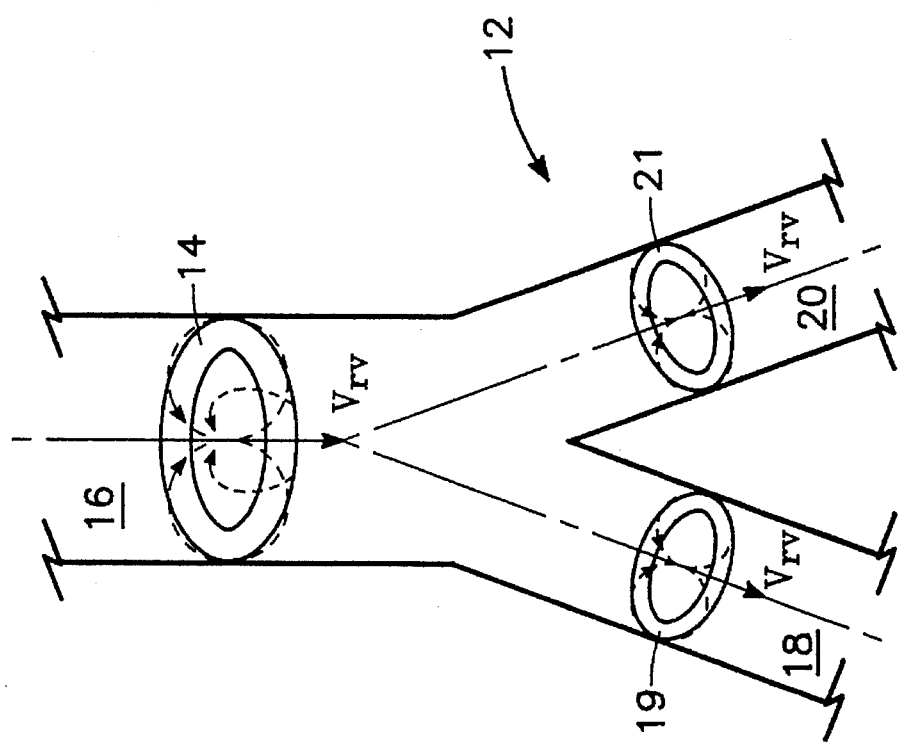
FIG. 2 illustrates a ring vortex of a medicated vapor entering the lungs of a patient and then splitting into a pair of ring vortices within the airways of the lung.
Figure 1:
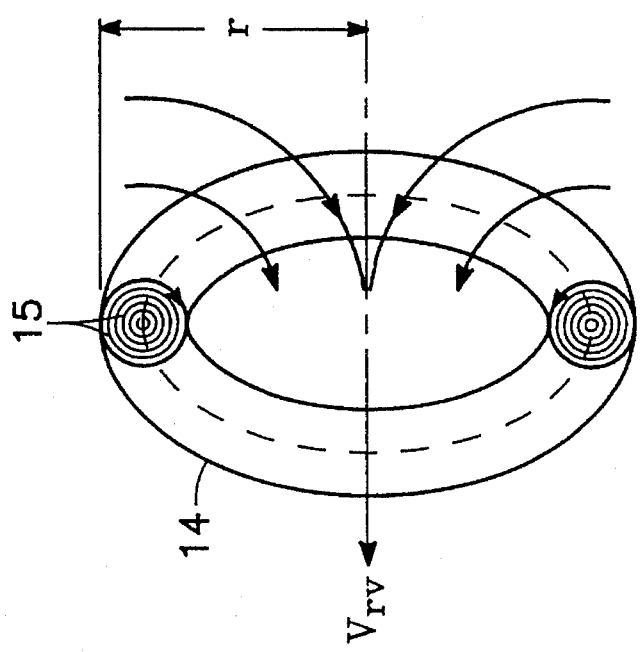
FIG. 1 is a sectional of a ring vortex of a medicated vapor formed by the aerosol dispensing apparatus constituting the present invention.
Figure 3B:
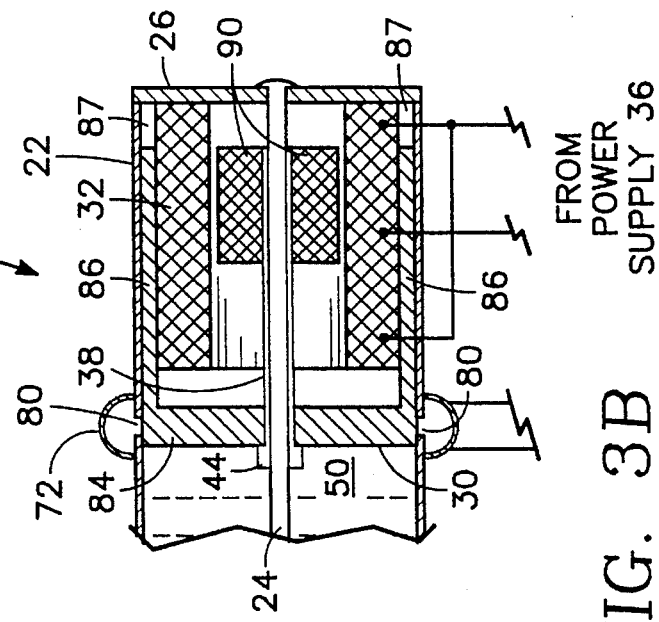
FIG. 3B is a alternate sectional view of the embodiment of FIG. 3A illustrating a solenoid driven reciprocating piston.
Figure 3A:
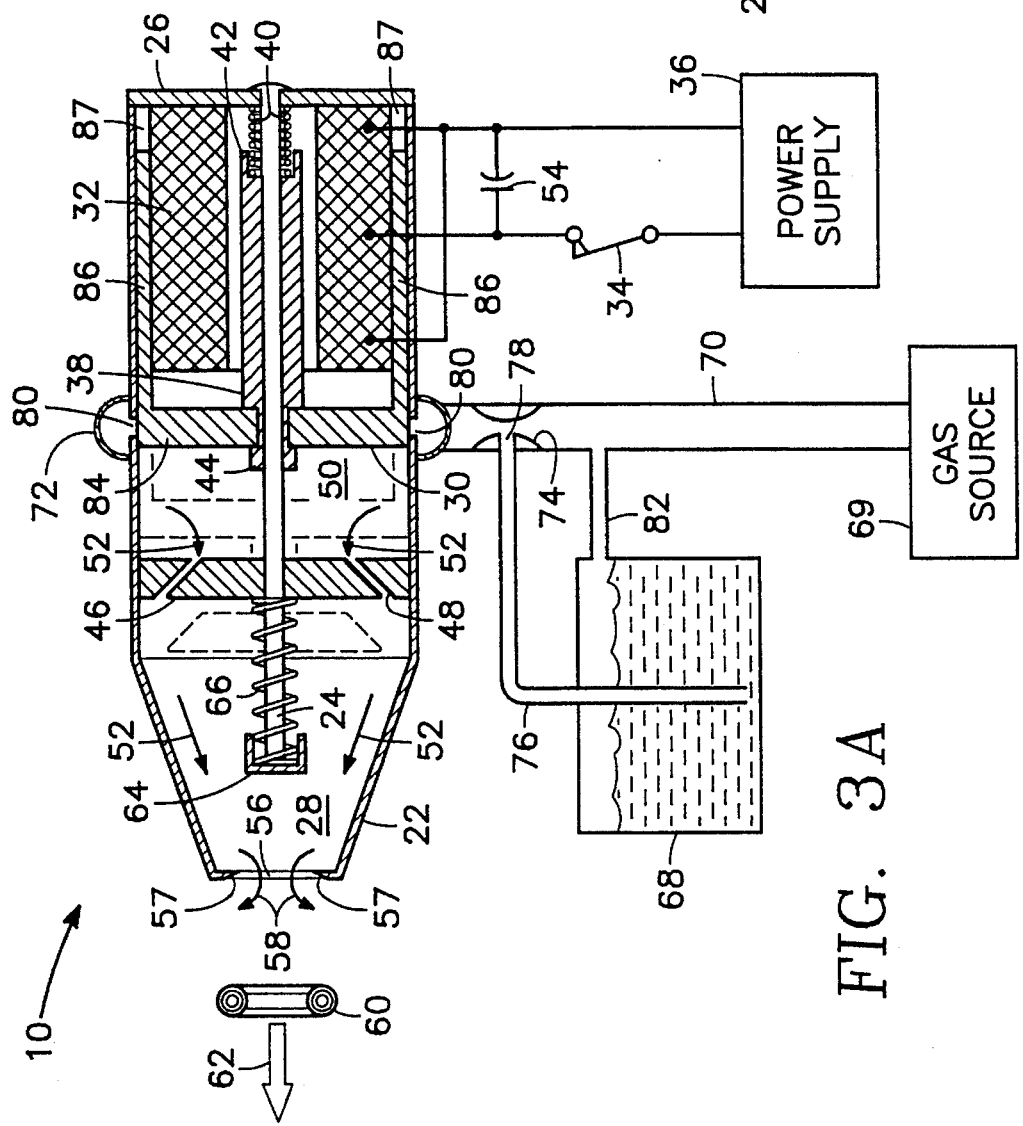
FIG. 3A is a sectional view of a preferred embodiment aerosol dispensing apparatus for providing a medicated vapor into the lungs of a patient.

Referring to FIGS. 1, 2 and 3A there is shown an aerosol dispensing apparatus, designated generally by the reference 10 for dispensing a medicated vapor into the lungs 12 of a patient. Dispensing apparatus 10 generates a train of ring vortices 14 which enter the bronchial tubes 16, 18 and 20 of the lungs providing a medicated mist or vapor to the lungs 12.

Referring to FIGS. 3A and 3B, apparatus 10 includes a generally cylindrical shaped housing 22 which has mounted in a center portion thereof a support rod 24 which extends longitudinally forward from the rear wall 26 of housing 22 to a wave shaping chamber 28 positioned at the front end of housing 22. Support rod 24 is fixedly attached and supported by the rear wall 26 of housing 22.

A solenoid driven reciprocating piston 30 is slidably mounted on support rod 24 and is activated by a wire wound coil 32 mounted in the rear portion of housing 22. Wire wound coil 32 is connected through a normally open electrical switch 34 to a power supply 36. Power supply 36 supplies a signal which approximates a square wave having a positive voltage (between 5 volts and 25 volts) of predetermined magnitude followed by zero volts. The frequency of the signal provided by power supply is variable and generally between twenty and one hundred cycles per second.

When switch 34 is closed power supply 36 alternatively energizes and de-energizes coil 32. Energizing coil 32 draws plunger 38 of reciprocating piston 30 in rearward direction toward the rear wall 26 of housing 22. Plunger 38 is fabricated of ferro-magnetic material (such as iron) which is pulled into the magnetic field generated by coil 32.

Figure 4A:
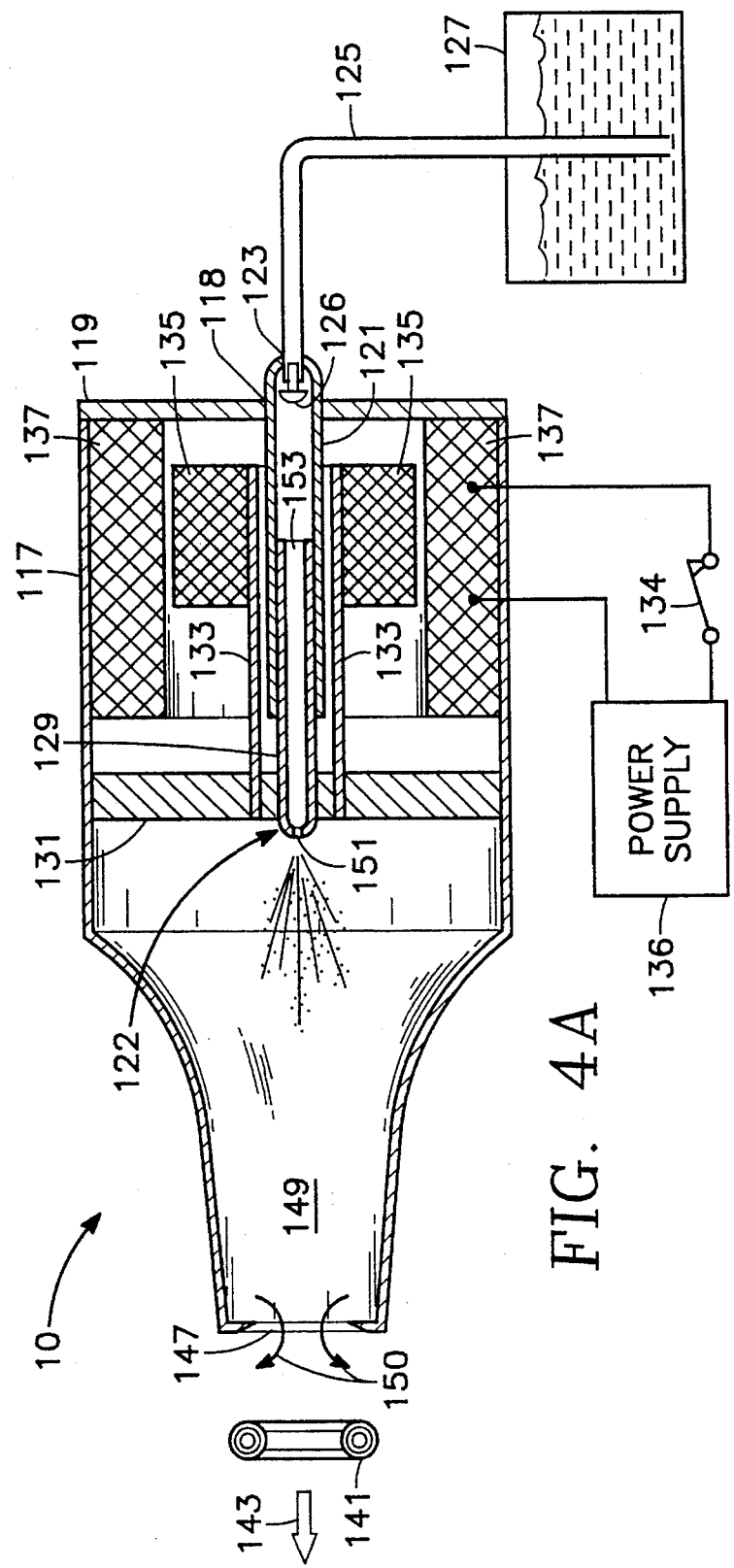
FIG. 4A is a second embodiment illustrated in section of the aerosol dispensing apparatus constituting the present invention.
Figure 4B:
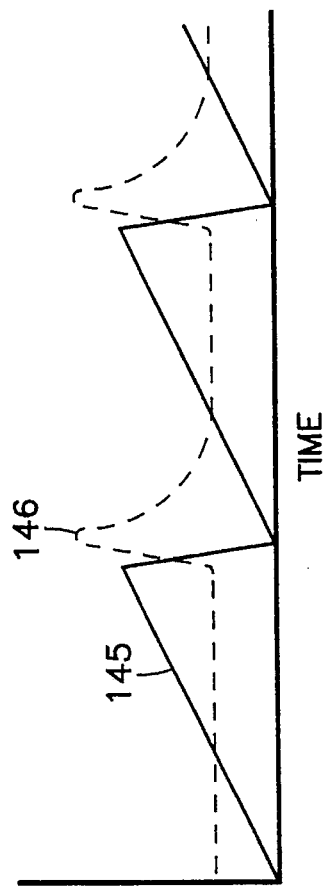
FIG. 4B illustrates voltage and pressure waveforms occurring within the apparatus of FIG. 4A.

As plunger 38 is drawn toward the rear wall 26 of housing 22 a spring 40 is compressed. Spring 40 is positioned around guide rod 24 between the inner surface of rear wall 26 and a spring seat 42 located at the rear end of plunger 38. When power supply 36 supplied zero volts to coil 32 de-energizing coil 32, plunger 38 is released from the magnetic field generated by coil 32. Spring 40, which is now fully compressed, exerts a force on plunger 38 thrusting plunger 38 in a forward direction (as illustrated in phantom in FIGS. 3A and 3B). A centrally positioned impact head 44 which is attached to the front end of reciprocating piston 30 next impacts a blast valve 46 unseating blast valve 46 from a valve seat 48. Unseating blast valve 46 allows medicated vapor compressed or pressurized within a centrally located chamber 50 to escape from chamber 50 through the opening formed between valve seat 48 and blast valve 46 into chamber 28 in the direction indicated generally by the arrows 52. The medicated vapor then exits a sharp edged orifice 56 positioned at the front end of housing 22 (as indicated by arrows 58 in FIG. 3A) forming a train of ring vortices 60. The train of ring vortices 60 travels in the direction indicted by arrow 62 entering the lungs 12 with medicated vapor. It should be noted orifice 56 which has a sharp or angled edge 57 functions as a sonic nozzle at the front end of aerosol dispensing apparatus 10 allowing apparatus 10 to generate the train of ring vortices 60 of medicated vapor.

There is positioned around support rod 24 between a spring seat 64 and blast valve 46 a spring 66 which applies a force against blast valve 46 maintaining blast valve 46 against valve seat 48 until valve 46 is unseated by reciprocating piston 30.

When reciprocating piston 30 is fully pulled rearward, that is retracted within housing 22 by coil 32, medicated vapor is supplied to chamber 50 within dispensing apparatus 10 from a reservoir 68 of liquid medication. Oxygen under pressure from a source 69 is supplied through a passageway 70 to a mist input manifold 72 which is positioned around the outer surface of housing 22. As the oxygen passes through a venturi 74 liquid medication from reservoir 68 is drawn through a passageway 76 and then through an opening 78 within venturi 74 mixing with the oxygen to form the medicated vapor being supplied to chamber 50. The medicated vapor enters chamber 50 from mist input manifold 72 via a plurality of inlet ports 80 positioned within and around housing 22 between the inner portion of manifold 72 and chamber 50.

It should be noted that aerosol dispensing apparatus 10 includes a second passageway 82 for connecting reservoir 68 to passageway 70. Passageway 82, in turn, provides for pressure equalization between reservoir 68 and passageway 70. It also be noted that air from the atmosphere instead of oxygen may be used with dispensing apparatus 10.

Reciprocating piston 30 also has a vertical extending support member 84 attached to the front end of plunger 38. Support member 84 forms the movable rear wall of chamber 50, while the combination of blast valve 46 and valve seat 48 form the front wall of chamber 50. Attached near the edge of support member 84 at its back side is a generally cylindrical shaped thin walled skirt 86 which extends into a recess 87 located between the inner surface of housing 22 and coil 32. The thin walled skirt 86, in turn, fits flush against the inner surface of housing 22.

When coil 32 is de-energized, spring 42 thrusts reciprocating piston 30 in a forward direction causing support member 84 and then skirt 86 to block inlet ports 80 which prevents medicated vapor from entering the interior of housing 22. When power supply 36 provides another positive voltage signal to coil 32 again energizing coil 32 piston 30 is retracted opening the inlet ports from mist input manifold 72 to chamber 50 allowing medicated vapor to again enter chamber 50.

An alternative embodiment of the dispensing apparatus 10 of FIG. 3A is illustrated in FIG. 3B. The dispensing apparatus 10 of FIG. 3B includes a permanent magnet 90 attached to the plunger 38 of reciprocating piston 30. A sinusoidal waveform signal is supplied by power supply 36 through switch 34. The magnetic field generated by coil 32 interacts with permanent magnet 90 causing reciprocating piston 30 to move forward and then backward at the frequency of the sinusoidal waveform signal supplied to coil 32 by power supply 36. This reciprocating motion of piston 30, in turn, results in the generation of the train of ring vortices 60 which have medicated vapor therein. A tuning capacitor 54 (illustrated in FIG. 3A) is also provided to fine tune the sinusoidal output signal from power supply 36.

Referring to FIG. 4A there is shown a detailed sectional of a third embodiment of dispensing apparatus 10. Dispensing apparatus 10 comprises a generally cylindrical shaped housing 117 having a rear wall 119. Passing through an aperture 118 at the center of rear wall 119 and extending from rear wall 119 into housing 117 is a cylindrical shaped pump housing 121 of a pump 122. Pump housing 121 of pump 122 extends longitudinally into the interior portion of housing 117 approximately a third of the length of housing 117. The end of pump housing 121 extending outside of dispensing apparatus 10 has an aperture 123 which receives one end of a passageway 125. A check valve 126 is also provided at this end of passageway 125. The opposite end of passageway 125 is connected to a reservoir 127 of liquid medication.

The pump plunger 129 of pump 122 is slidably mounted within pump housing 121 and is attached to a reciprocating piston 131 at the end thereof which extends from pump housing 121. A permanent magnet 135 is attached to the plunger 133 of reciprocating piston 131. Permanent magnet 135 is, in turn, positioned within the magnetic field generated by a coil 137 which is exited by a power supply 136 when a switch 134 is in the closed position.

When switch 134 is closed power supply 136 supplies a voltage signal 145 (FIG. 4B) to the coil 137 of dispensing apparatus 10. The voltage signal 145 first ramps to a predetermined DC voltage (between about 5–25 VDC) causing piston 131 to move slowly toward the rear wall 119 and then drops suddenly to 0 VDC causing rapid movement of piston 131 in a forward direction.

When piston 131 moves slowly rearward check valve 126 closes and liquid medication within the interior portion 153 of pump 122 passes through a nozzle 151 at the end of pump plunger 129 into a mixing chamber 149. Rearward movement of piston 131 also draws air from the atmosphere through a sharp edge orifice 147 at the front end of housing 117 into mixing chamber 149.

The air then mixes with the liquid medication in the mixing chamber 149 to form a medicated vapor. The rapid forward movement of piston 131 expels the medicated vapor under pressure (waveform 146, FIG. 4B) which may exceed 400 psi from mixing chamber 149 through sharp edged orifice 147 (in the manner illustrated by arrows 150) forming the ring vortex 141. Ring vortex 141 then travels in the direction indicated by arrow 143 into the lungs of a patient.

The rapid forward movement of piston 131 also opens check valve 126 causing liquid medication to be withdrawn from reservoir 127 through passageway 125 into the interior portion 153 of pump 122.

Referring to FIG. 5 there is shown a detailed sectional view of a fourth embodiment of dispensing apparatus 10. Dispensing apparatus 10 comprises a housing 217 having a centrally located shaft 218 which extends the length of housing 217 through the rear of housing 217. Shaft 218 has hollow inner portion 219 and is coupled to a reservoir 268 of medicated liquid by a passageway 270 and a mist generator 271. Mist generator 271 is positioned within shaft 218 near the rear end of shaft 218.

When a switch 272 is closed a power supply 274 supplies a direct current voltage signal to a solenoid valve 276 energizing solenoid valve 276 which opens valve 276. Opening valve 276 allows oxygen, for example, or air from the atmosphere under pressure from an external source 292 to pass through valve 276 and then enter mist generator 271 via a passageway 278 which extends into the interior of nozzle 271. Pressurized oxygen exits passageway 278 through an opening 282 into an interior portion 284 of mist generator nozzle 271. Liquid medication from reservoir 268 is drawn into the interior portion of mist generator 271 because passageway 273 is under pressure which provides for pressurization of reservoir 268. The pressurized oxygen or air from the atmosphere then mixes with the liquid medication forming a medicated vapor which exits an orifice 290 (under pressure) of nozzle 271 into the hollow inner portion 219 of shaft 218.

Shaft 218 has a plurality of openings 221 which allow pressurized medicated vapor to enter a charging chamber 220 within housing 217. There is located within housing 217 at the rear of chamber 220 an inner wall 241 which includes a plurality of openings 222 which allows pressurized medicated vapor to bleed from chamber 220 into a rear chamber 237 located at the rear of housing 217.

Chamber 237 includes a diaphragm 223 mounted therein. Diaphragm 223 is secured at its outer edge to housing 217. Shaft 218 has a cylindrical support bracket 238 positioned about its outer surface in slidable engagement with its outer surface. A flange 240 at one end of cylindrical support bracket 238 secures diaphragm 223 to bracket 238. The opposite end of cylindrical support bracket 238 has attached thereto a blast valve 225 which is maintained under pressure against a valve seat 226 within housing 217 by both pressure and a spring 224 positioned around shaft 218 between valve 225 and inner wall 241.

Inner wall 241 has an aperture 235 through which support bracket 238 passes, while the rear wall 243 of housing 217 has an aperture 244 through the rear portion of shaft 218 passes. Aperture 235 of inner wall 241 and aperture 244 of rear wall 243 provide support for 218 and also allow for movement of bracket 238 within housing 217 of dispensing apparatus 10.

When the pressure of the medicated vapor within chamber 237 reaches about 400 psi the force exerted upon diaphragm 223 will exceed the tension maintained against valve 225. Diaphragm 223 will then move rearward within chamber 237 causing cylindrical support bracket 238 to move in rearward direction which unseats blast valve 225 from valve seat 226 within housing 217.

At this time it should be noted that the preferred embodiment of the present invention has four openings within shaft 218 each of which has a diameter of about ½ inch, while inner wall 241 also has four openings 222 each of which has a diameter of about ¼ inch. This, in turn, results in an area ratio of about four to one which insures that there will be a sufficient amount of pressurized medicated vapor entering chamber 237 to exert enough pressure on diaphragm 223 to move diaphragm 223 in a rearward direction to unseat valve 225 from valve seat 226 allowing pressurized gas to escape from chamber 220 into a wave shaping chamber 227 located at the front portion of housing 217.

Inner wall 241 also includes a pair of ports 236 each of which has a check valve 234. When blast valve 225 unseats from valve seat 226 of housing 217 pressurized medicated vapor escapes from chamber 220 into chamber 227 substantially reducing the pressure within chamber 220 so that there is a pressure differential between chambers 237 and 220. This pressure differential opens check valves allowing the medicated vapor within chamber 237 to pass through ports 236 into chamber 220. The reduction of pressure within chamber 237 allows check valves 234 to close and also allows diaphragm 223 and bracket 238 to return to a neutral position (illustrated by FIG. 5) which seats blast valve 225 against valve seat 226 allowing dispensing apparatus 10 to repeat this cycle to generate another ring vortex 216 of medicated vapor.

Medicated vapor under pressure will again enter chamber 220 via openings 221 within shaft 218 and bracket 238 and then pass through openings 222 until the pressure within chamber 237 exceeds 400 psi at which time diaphragm 223 is forced rearward causing pressurized medicated vapor to escape from chamber 220 into wave shaping chamber 227. This reduces the pressure within chamber 220 opening check valves 234 (illustrated in the open position in FIG. 5) which allows diaphragm 223 to return to its neutral position. When diaphragm 223 returns to its neutral position, blast valve 225 seats against valve seat 226 sealing off chamber 220 from chamber 227. The opening and closing of blast valve 225 is repeated at a frequency of between 20 and 100 hertz, that is between about twenty cycles per second and about 100 cycles per second.

At this time it should be noted that the rear wall 243 of housing 217 has a plurality of apertures 239 which allow air from the atmosphere to either exit the rear portion of chamber 237 into the atmosphere when diaphragm 223 is forced in a rearward direction or enter chamber 237 when diaphragm 223 returns to its neutral position.

When blast valve 225 unseats from housing 217 pressurized medicated vapor escapes from chamber 220 into wave shaping chamber 227 in the manner illustrated by arrows 245. Housing 217 has at its front end a ring vortex shaping structure, designated generally by the reference numeral 228. Ring vortex shaping structure 228 includes a shaping member 246 attached to the front of shaft 218 having an outer symmetrical surface 247 which along with surface 288 functions as a supersonic nozzle at the front end of aerosol dispensing apparatus 10. The front end 248 of housing 217, which approximates a cylinder, has a curved inner surface 249. There is positioned between the inner curved surface 249 of housing 217 and the outer symmetrical surface 247 of shaping member 246 a shaping member 285. Shaping member 285 is, in turn, secured to housing 217 by a plurality of streamlined support blades 286.

Figure 5:
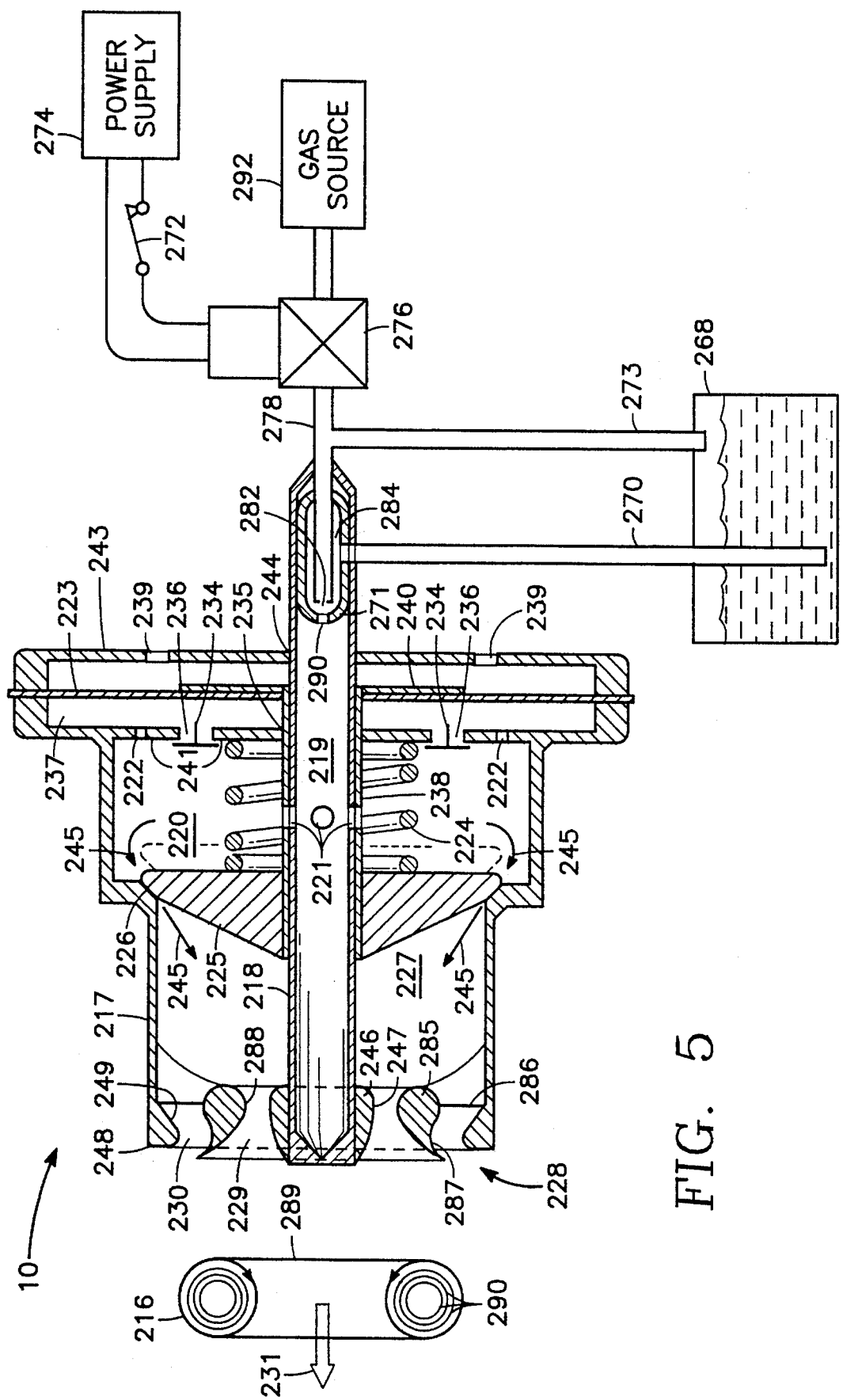
FIG. 5 is a third embodiment illustrated in section of the aerosol dispensing apparatus constituting the present invention.

Shaping member 285 has a concave outer surface 287 which parallels inner surface 249 of housing 217 (as is best illustrated in FIG. 5) forming an outer annular port 230. Shaping member 285 has a curved inner surface 288 which with the outer surface of shaping member 246 forms an inner annular supersonic port 229. Medicated vapor entering wave shaping chamber 227 under pressure is accelerated towards annular ports 229 and 230 which, in combination, form the ring vortexes 216.

Referring to FIGS. 1 and 5, FIG. 1 illustrates a cross sectional view of ring vortex 14 (reference numeral 216 in FIG. 5) formed by medicated vapor exiting from chamber 227 through annular ports 229 and 230 into the lungs of a patient. Annular port's 229 size and shape accelerates the expanding medicated vapor puffs to subsonic velocities in the order of between about 1500 ft/sec to 2000 ft/sec. Annular port 230 is shaped to provide an outer lamina 289 for each puff of medicated vapor exiting dispensing apparatus 10. Each resultant puff of high speed medicated vapor is formed into a ring vortex 216 with high aerodynamic circulation. Ring vortex 216 travels at high subsonic speed (typically about 900 feet per second) in the direction indicated generally by arrow 231 into the lungs of a patient. Each ring vortex 216 is represented by a plurality of concentric streamlines 290 centered about the vortex core of medicated vapor.

Figure 6:
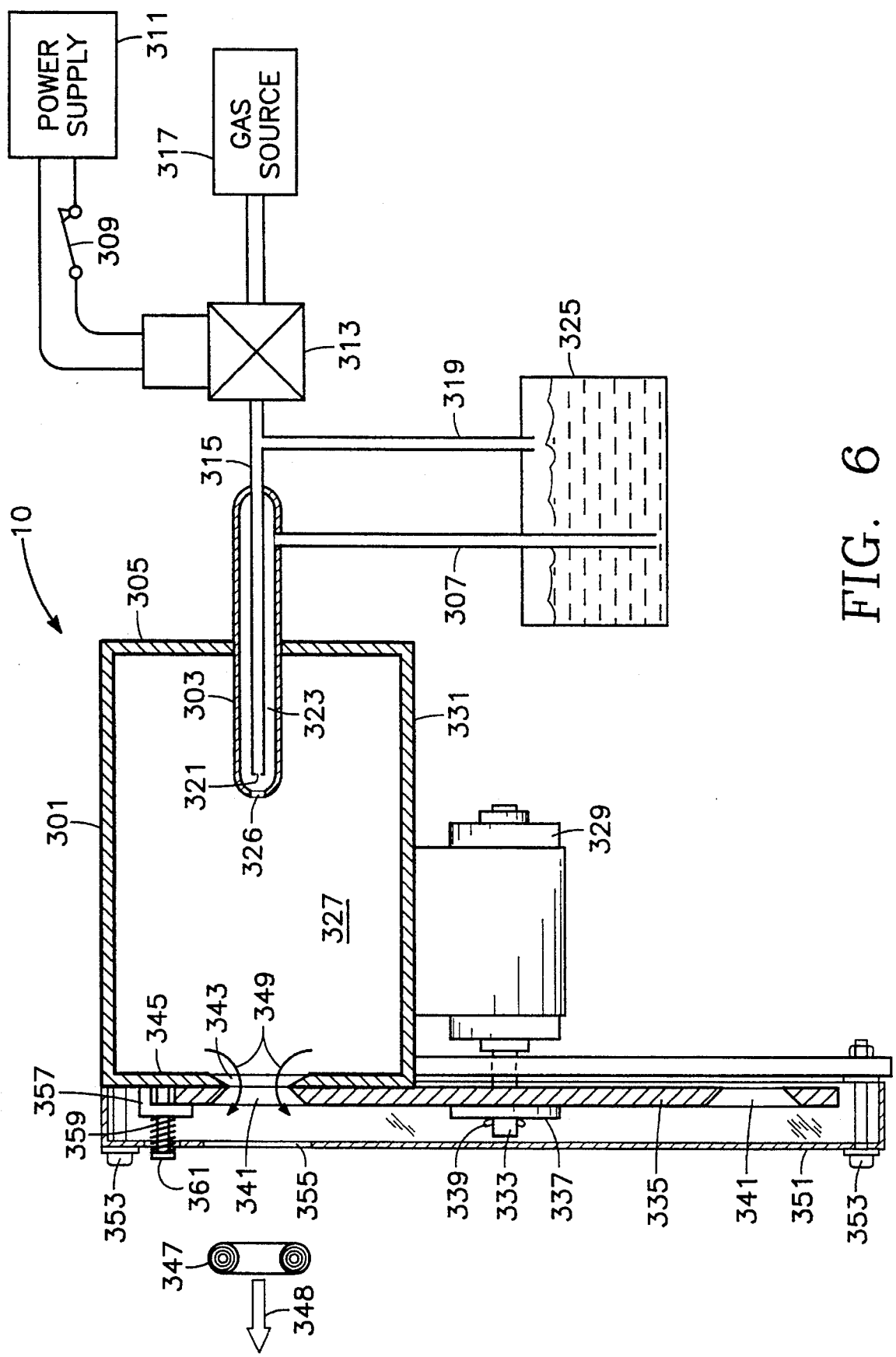
FIG. 6 is a fourth embodiment illustrated in section of the aerosol dispensing apparatus constituting the present invention.

Referring to FIG. 6, there is shown a detailed sectional view of a fifth embodiment of dispensing apparatus 10. Dispensing apparatus 10 comprises a housing 301 having a centrally located vapor forming structure 303 which extends partially into housing 301 through and from the rear wall 305 of housing 301. Vapor forming structure 303 is connected by a passageway 307 to a reservoir 325 of medicated liquid.

When a switch 309 is closed a power supply 311 supplies a direct current voltage signal to a solenoid valve 313 energizing solenoid valve 313 which opens valve within solenoid valve 313. Opening valve 313 allows oxygen or air from the atmosphere under pressure from an external source 317 to pass through valve 313 and then enter vapor forming structure 303 via a passageway 315 which extends into the interior of structure 303.

Pressurized oxygen exits passageway 315 through an opening 321 into an interior portion 323 of vapor forming structure 303. Liquid medication is drawn from reservoir 325 into the interior portion 323 of vapor forming structure 303 since passageway 319 is pressurized. The pressurized oxygen then mixes with the liquid medication forming a medicated vapor which exits an orifice 326 (under pressure) of vapor forming structure 303 into charging chamber 327.

A motor 329 is mounted on a side wall 331 of housing 301. The shaft 333 of a motor 329 is secured to a disk 335 by a washer 337 and a coupling pin 339. Disk 335 has four equally spaced sharp edged orifices 341 (spaced approximately 90 degrees apart). Each of the four sharp edged orifices 341 of disk 335 are positioned near the periphery of disk 335 to align with a sharp edged orifice 343 in the front wall 345 of housing 301.

When energized motor 329 rotates disk 335 at a speed sufficient to allow for repeated alignment of one of the four sharp edged orifices 341 of disk 335 with sharp edge orifice 343 at a frequency of at least twenty times per second. When one of the four sharp edged orifices 341 of disk 335 aligns with sharp edge orifice 343 a ring vortex of medicated vapor 347 is generated in the manner illustrated by arrows 349. The ring vortex 347 then travels in the direction indicated by arrow 348 into the lungs of a patient.

The dispensing apparatus 10 also has a cover plate 351 secured to its front end to protect disk 335. A plurality of bolts 353 secure cover plate 351 to dispensing apparatus 10. Cover plate 351 also has an opening 355 which is in alignment with sharp edge orifice 343 allowing each ring vortex of medicated vapor 347 to pass through cover plate 351.

An L shaped clamp 357 and spring 359, secured to wall 345 by a screw 361, maintain a pressure seal between each sharp edged orifice 341 of disk 335 and sharp edge orifice 343 when the orifices are aligned.

Figure 7:
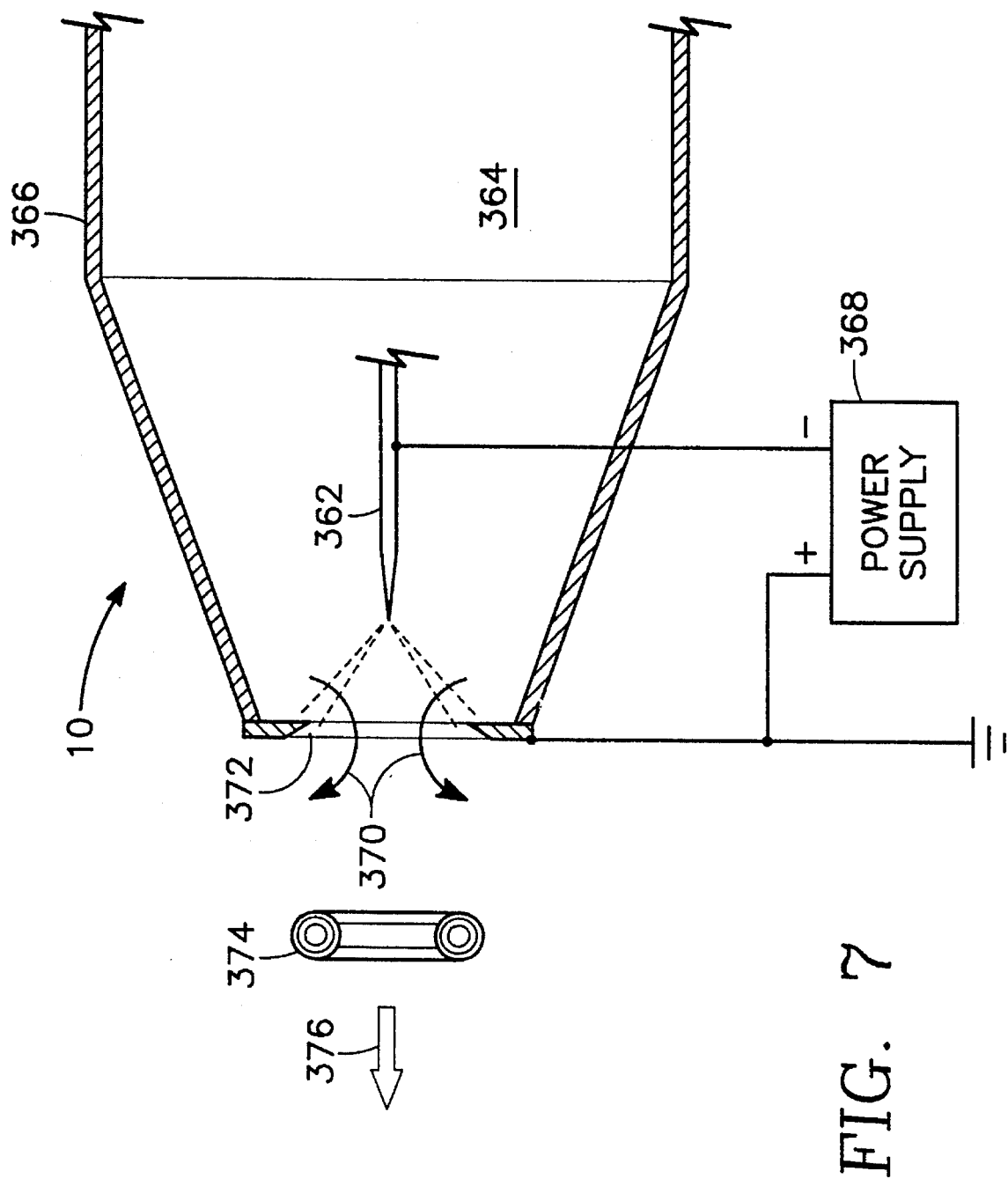
FIG. 7 is a partial sectional view of a needle electrode assembly for providing charges to the ring vortices generated by the aerosol dispensing apparatus of the present invention.

Referring now to FIG. 7, there is shown a needle electrode 362 mounted in a mixing chamber 364 at the forward end of housing 366 of dispensing apparatus 10. Needle electrode 362 is connected to the negative terminal of a power supply 368, while the positive terminal of power supply is connected to the housing 366 of dispensing apparatus 10. Power supply 368 supplies a negative direct current voltage of several thousand volts (at least 2000–5000 VDC) which ionizes droplets of the medicated vapor within mixing chamber 364. The ionized vapor then exits chamber 364 (as indicted by arrows 370) through sharp edged orifice 372 forming the ionized ring vortex 374. The negatively ionized ring vortex 374 then travels in the direction indicated by arrow 376 entering the lungs of a patient.

It should be noted that the purpose of ionizing the medicated vapor is to enhance attachment of droplets of medicated vapor to the inner walls 16, 18 and 20 of the lungs 12 (FIG. 2) of a patient by electrostatic attraction.

Referring now to Fig.8, there is shown a mask and support assembly 380 which includes a mask 382 adapted to cover the mouth 384 and nose 386 of a patient 388. The mask 382 is secured to the patient by means of an elastic strap 390. Apparatus 10 is mounted on the mask 382 (in the manner illustrated in FIG. 8) so as to provide to the patient a train of ring vortices 14 (FIGS. 1 and 2) which enter the patient's lungs 12 (FIG. 2) through his mouth 384 and nose 386 when the patient inhales. The mask and support assembly may also include a flexible hose 392 which connects the reservoir 68 (FIG. 3A) of liquid medication and the gas source 69 (FIG. 3A) and a sensing switch 394 which turns on dispensing apparatus 10 when the patient inhales.

An approximate relationship governing the structure, vortex strength and propagation velocity of a ring vortex (such as the ring vortices 14 illustrated in FIGS. 1 and 2) is the Biot-Savart formula which may be expressed as follows.

$$V_{rv} = \frac{\Gamma}{2\pi r}$$

where, $V_{rv}$ is the velocity of ring propagation through air, $\Gamma$ is the vortex strength, and r is the radius of the ring at the vortex core.

Vortex strength $\Gamma$ (referred to as circulation) is defined as a closed integral of the tangential velocity component around a vortex core. For a ring vortex by the following relationship is applicable.

$$\Gamma = 2\pi r' u_\Theta$$

here $u_\Theta$ is a tangential component of vortex velocity along a circle of constant radius r'.

Vortex strength is a function of charging chamber pressure, that is pressure in chamber 50 (FIG. 3A), the expansion ratio in the ring vortex forming section, that is chamber 28 (FIG. 3A), and the specific characteristics of the gas being used by dispensing apparatus 10. By selecting appropriate temperature and pressure values of a gas such as the medicated vapor for use with dispensing apparatus 10 and appropriate projector dimensions for apparatus 10, the strength and velocity of the ring vortex may be determined as well as varied to meet the requirements of an individual using the gas projection apparatus of the present invention.

From the foregoing, it may readily be seen that the present invention comprises a new, unique and exceedingly useful aerosol dispensing apparatus for effectively providing medication in a mist or vapor form to the lungs of a patient which constitutes a considerable improvement over the known prior art. Obviously many modifications and variations of the present invention are possible in light of the above teachings. It is therefore to be understood that within the scope of the appended claims, the invention may be practiced otherwise than as specifically described.

What is claimed is:

1. An aerosol dispensing apparatus comprising:

a reservoir for providing a medication under pressure;

a cylindrical shaped housing having a centrally located chamber and a rear wall;

a wave shaping chamber located in a front portion of said housing, said wave shaping chamber being adjacent said centrally located chamber;

a blast valve resting on a valve seat located within said housing, said blast valve being interposed between said centrally located chamber and said wave shaping chamber to seal said centrally located chamber from said wave shaping chamber;

a support rod centrally located within said housing, said support rod fixedly attached to the rear wall of said housing, said support rod extending longitudinally forward from the rear wall of said housing;

a piston having a plunger slidably mounted on said support rod and a vertical extending support member attached to the front end of said plunger, said support member forming a movable rear wall of said centrally located chamber;

an impact head attached to the front end of said piston;

a coil mounted within a rear portion of said housing;

the support member of said piston having a cylindrical shaped skirt attached thereto, said cylindrical shaped skirt extending into a recess located between the inner surface of said housing and said coil;

a power supply connected to said coil, said power supply providing a square wave signal of a predetermined frequency to alternatively energize and de-energize said coil, said coil when energized drawing said piston in a rearward direction, said piston moving in a forward when said coil is de-energized;

an input manifold positioned around an outer surface of said housing, said input manifold being coupled to said reservoir for receiving said liquid medication from said reservoir;

a plurality of inlet ports positioned around said housing between said manifold and said centrally located chamber, said medication entering said centrally located chamber as a medicated vapor through said plurality of inlet ports when said piston is drawn in said rearward direction, said inlet ports being closed by said cylindrical shaped skirt when said piston moves in said forward direction;

said impact head unseating said blast valve when said piston moves in said forwarding direction allowing said medicated vapor to enter said wave shaping chamber;

said housing having an edged shaped orifice at a front end thereof, said edged shaped orifice communicating with said wave shaping chamber allowing said medicated vapor to exit said wave shaping chamber and pass through said edged shaped orifice to form a ring vortex of medicated vapor;

said blast valve opening and closing at the predetermined frequency of said square wave signal causing said aerosol dispensing apparatus to generate a train of said ring vortices of medicated vapor; and a mask coupled to the front end of said housing, said mask being adapted to cover a patient's mouth and nose, said mask having an elastic band for securing said mask to said patient, said mask receiving the train of ring vortices of said medicated vapor allowing said patient to inhale the train of said ring vortices of medicated vapor.

2. The aerosol dispensing apparatus of claim 1 wherein said predetermined frequency of said square wave signal is between about twenty cycles per second and about one hundred cycles per second.

3. The aerosol dispensing apparatus of claim 1 further comprising a gas source coupled to said reservoir, said gas source providing a gas under pressure to said reservoir to pressurize said medication.

4. The aerosol dispensing apparatus of claim 3 wherein said gas under pressure comprises oxygen.

5. The aerosol dispensing apparatus of claim 1 further comprising a spring disposed around the outer surface of said support rod between the rear end of the plunger of said piston and the rear wall of said housing.

6. The aerosol dispensing of claim 1 further comprising a normally open electrical switch for connecting said power supply to said coil when said switch is closed.

7. An aerosol dispensing apparatus comprising:

a reservoir for providing a medication under pressure;

a cylindrical shaped housing having a centrally located chamber and a rear wall;

a wave shaping chamber located in a front portion of said housing, said wave shaping chamber being adjacent said centrally located chamber;

a blast valve resting on a valve seat located within said housing, said blast valve being interposed between said centrally located chamber and said wave shaping chamber to seal said centrally located chamber from said wave shaping chamber;

a support rod centrally located within said housing, said support rod fixedly attached to the rear wall of said housing, said support rod extending longitudinally forward from the rear wall of said housing, said support rod having a first spring seat;

a piston having a plunger slidably mounted on said support rod and a vertical extending support member attached the front end of said plunger, said support member forming a movable rear wall of said centrally located chamber, the rear end of said plunger having a second spring seat;

a first spring disposed around the outer surface of said support between said first spring seat and said blast valve;

a second spring disposed around the outer surface of said support rod between said second spring seat and the rear wall of said housing;

an impact head attached to the front end of said piston;

a coil mounted within a rear portion of said housing;

the support member of said piston having a cylindrical shaped skirt attached thereto, said cylindrical shaped skirt extending into a recess located between the inner surface of said housing and said coil;

a power supply connected to said coil, said power supply providing a square wave signal of a predetermined frequency to alternatively energize and de-energize said coil, said coil when energized drawing said piston in a rearward direction, said second spring exerting a force upon said piston moving said piston in a forward direction when said coil is de-energized;

an input manifold positioned around an outer surface of said housing, said input manifold being coupled to said reservoir for receiving said liquid medication from said reservoir;

a plurality of inlet ports positioned around said housing between said manifold and said centrally located chamber, said medication entering said centrally located chamber as a medicated vapor through said plurality of inlet ports when said piston is drawn in said rearward direction, said inlet ports being closed by said cylindrical shaped skirt when said piston moves in said forward direction;

said impact head unseating said blast valve when said piston moves in said forwarding direction allowing said medicated vapor to enter said wave shaping chamber;

said housing having an edged shaped orifice at a front end thereof, said edged shaped orifice communicating with said wave shaping chamber allowing said medicated vapor to exit said wave shaping chamber and pass through said edged shaped orifice to form a ring vortex of medicated vapor;

said blast valve opening and closing at the predetermined frequency of said square wave signal causing said aerosol dispensing apparatus to generate a train of said ring vortices of medicated vapor; and a mask coupled to the front end of said housing, said mask being adapted to cover a patient's mouth and nose, said mask having an elastic band for securing said mask to said patient, said mask receiving the train of ring vortices of said medicated vapor allowing said patient to inhale the train of said ring vortices of medicated vapor.

8. The aerosol dispensing apparatus of claim 7 wherein said predetermined frequency of said square wave signal is between about twenty cycles per second and about one hundred cycles per second.

9. The aerosol dispensing apparatus of claim 7 further comprising a gas source coupled to said reservoir, said gas source providing a gas under pressure to said reservoir to pressurize said medication.

10. The aerosol dispensing apparatus of claim 7 wherein said gas under pressure comprises oxygen.

11. The aerosol dispensing of claim 7 further comprising a normally open electrical switch for connecting said power supply to said coil when said switch is closed.

* * * * *